(12) United States Patent
Engel

(10) Patent No.: US 10,470,722 B2
(45) Date of Patent: Nov. 12, 2019

(54) SYSTEMS AND METHODS FOR GRATING MODULATION OF A SPECTRA AND INTENSITY IN COMPUTED TOMOGRAPHY

(71) Applicant: KONINKLIJKE PHILIPS N.V., Eindhoven (NL)

(72) Inventor: Klaus Jürgen Engel, Veldhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 233 days.

(21) Appl. No.: 15/506,959

(22) PCT Filed: Sep. 1, 2015

(86) PCT No.: PCT/IB2015/056617
§ 371 (c)(1),
(2) Date: Feb. 27, 2017

(87) PCT Pub. No.: WO2016/038504
PCT Pub. Date: Mar. 17, 2016

(65) Prior Publication Data
US 2017/0273642 A1    Sep. 28, 2017

Related U.S. Application Data

(60) Provisional application No. 62/047,127, filed on Sep. 8, 2014.

(51) Int. Cl.
*G01N 23/04*    (2018.01)
*A61B 6/00*    (2006.01)
(Continued)

(52) U.S. Cl.
CPC .......... *A61B 6/032* (2013.01); *A61B 6/4007* (2013.01); *A61B 6/4021* (2013.01);
(Continued)

(58) Field of Classification Search
CPC ..... A61B 6/032; A61B 6/4007; A61B 6/4021; A61B 6/4035; A61B 6/482; A61B 6/00;
(Continued)

(56) References Cited

U.S. PATENT DOCUMENTS

| 3,950,613 A | 4/1976 | Macovski |
| 2003/0089857 A1 | 5/2003 | Hoheisel et al. |

(Continued)

FOREIGN PATENT DOCUMENTS

| KR | 20120013724 | 2/2012 |
| WO | 2010/055930 | 5/2010 |
| WO | 2012/032435 | 3/2012 |

*Primary Examiner* — Irakli Kiknadze
(74) *Attorney, Agent, or Firm* — Larry Liberchuk

(57) ABSTRACT

An X-ray imaging system for generating X-ray projections of an object, the X-ray imaging system including an X-ray device having a single X-ray source (110) for forming a plurality of X-ray beams (104), a filter (120) positioned within the plurality of X-ray beams, an object space where the object to be imaged is accommodated, and an X-ray detector (150) including an array of a plurality of pixels (151 . . . 155). The X-ray device, the filter, and the plurality of pixels are configured such that at least one pixel is exposed to the plurality of X-ray beams. X-ray radiation received by a particular pixel undergoes a same spectral filtration by the filter. Pixels receiving the X-ray radiation undergoing the same spectral filtration are summarized to a pixel subset.

20 Claims, 5 Drawing Sheets

(51) Int. Cl.
*A61B 6/03* (2006.01)
*G01N 23/087* (2018.01)
*G21K 1/10* (2006.01)

(52) U.S. Cl.
CPC ............ *A61B 6/4035* (2013.01); *A61B 6/482* (2013.01); *G01N 23/087* (2013.01); *G21K 1/10* (2013.01); *G01N 2223/419* (2013.01)

(58) Field of Classification Search
CPC ..... A61B 6/4028; A61B 6/405; A61B 6/4233; A61B 6/06; A61B 6/40; A61B 6/4042; A61B 6/4078; A61B 6/03; A61B 6/4258; A61B 6/5205; A61B 6/5258; G01N 23/087; G01N 2223/419; G01N 23/046; G21K 1/10; H01J 2235/062; H01J 2235/068; H01J 2235/087; H01J 35/065; H01J 35/08; G06T 2207/10116; G06T 2207/30004; G06T 5/008; G06T 5/40; G06T 7/0012; G06T 7/12; G06T 7/194; G06T 11/006; G06T 2211/421; G06T 2211/436
USPC ................ 378/62, 147, 148, 156–160, 4, 19
See application file for complete search history.

(56) References Cited

U.S. PATENT DOCUMENTS

| | | |
|---|---|---|
| 2005/0117701 A1* | 6/2005 | Nelson ................. G01N 23/203 378/87 |
| 2007/0133749 A1 | 6/2007 | Mazin |
| 2009/0232270 A1 | 9/2009 | Okunuki |
| 2013/0156157 A1 | 6/2013 | Engel |

* cited by examiner

SYSTEMS AND METHODS FOR GRATING MODULATION OF A SPECTRA AND INTENSITY IN COMPUTED TOMOGRAPHY

CROSS REFERENCE TO RELATED APPLICATIONS

This application is the U.S. National Phase application under 35 U.S.C. § 371 of International Application No. PCT/IB2015/056617, filed Sep. 1, 2015, published as WO 2016/038504 on Mar. 17, 2016, which claims the benefit of U.S. Provisional Patent Application No. 62/047,127 filed Sep. 8, 2014. These applications are hereby incorporated by reference herein.

BACKGROUND

Technical Field

The present disclosure relates to a method and an imaging system for generating spectrally different X-ray images with an X-ray source and an X-ray detector. More particularly, the present disclosure relates to including a filter providing different spectral filtration within an X-ray system in order to produce a spectrally modulated beam such that neighboring pixels of the X-ray detector receive different spectra, and using this spectral information to perform means of spectral X-ray imaging.

Description of Related Art

Computed tomography (CT) is the science of recovering a three-dimensional representation of a patient or object by utilizing projection views with different orientations. From this volume, e.g., two-dimensional cross-sectional images can be displayed. CT systems typically include an X-ray source collimated to form a cone beam directed through an object to be imaged, i.e., a patient, and received by an X-ray detector array. The X-ray source, the cone beam, and the detector array may be rotated together on a gantry within the imaging plane, around the imaged object.

However, the X-ray radiation imposes unwanted effects. In the medical imaging domain, an unwanted effect may be the radiation dose that a patient receives, as it may induce damage to cells and genes. As a further unwanted effect, the interaction of X-ray radiation with matter imposes scattered X-ray radiation, which adds in the detector to the signal of interest, i.e., the signal of the primary radiation. As a most obvious method to reduce the unwanted effects, measures are taken to limit the amount of total X-ray exposure to a minimum, which is required to acquire images.

To reduce the negative effects, three elements are used to form the cone beam. First, a collimator defines a cone shape such that the cone beam covers exactly the whole detector area in order that each detector imaging element (denoted herein as a "pixel") is exposed to the beam, but the overlap to the non-detector area is reduced to a minimum. Second, a bowtie-shaped device, known as a "beam shaper," "bow tie" or sometimes also as a "wedge," is placed in the path of the X-ray beam. The wedge, functioning as an X-ray attenuation filter, is generally made of a light metal, such as aluminum, or a synthetic polymer, such as Teflon, having an X-ray absorption spectral characteristic near that of water, and, hence, the human body.

The wedge is intended to compensate for the variation in thickness of the imaged body. The X-rays that pass through the center of the imaged body, normally the thickest part, are least attenuated by this filter, whereas the X-rays that pass through the periphery of the imaged body, normally the thinnest part, are more attenuated by this filter. The result of this selective attenuation is a better distribution of the X-ray dose.

This allows, on one hand, for a total dose reduction for the scanned patient. On the other hand, the X-rays impinging on the detectors have a less spatially varying intensity profile. The wedge may therefore allow use of more sensitive X-ray detectors, thus reducing the total dynamic range of x-ray intensities to be detected. Finally, as a third element to reduce negative effects, a spatially homogeneous filter (typically in the form of a metal plate, e.g., made of copper) is induced to absorb mainly the low energy components of the spectrum. The low energy components of the plain X-ray spectrum are typically that strongly attenuated by an object or a patient that they do not significantly contribute to a measured signal. Thus, the filter reduces the total dose a patient is exposed to with an acceptable reduction of the acquired detector signal.

Next, it is also desired to reduce scattered X-ray radiation to a minimum, as its intensity overlays to the primary intensity and therefore induces image artifacts due to a higher intensity measured. It is therefore desirable to develop methods to determine the amount of scattered radiation so as to correct the measured radiation for the scattered radiation signal. Typically the scattered radiation cannot easily be accessed as it is a priori not distinguishable from the primary radiation. Further, it is also difficult to determine it from the whole context of an acquired image as scattered radiation is related to the scanned patient geometry in a complex manner.

Special aspects of CT are spectral methods commonly termed as dual energy CT, multi-energy CT, or spectral CT. The common characteristic of all these methods is that they take use of the fact that different materials attenuate X-rays differently with respect to the energy of the X-ray photons. Consequently, the acquisition of CT projections with different weightings put on the X-ray photon energies provides additional (3D) information, not only of the material density, but also of the chemical composition. In other words, if it is possible to scan an object volume with data sets representing different spectral weightings, it becomes possible to apply mathematical methods to generate a 3D data volume representing different physical or chemical properties. Commonly known examples for such properties are the ratio of bone mineral density to soft tissue density, or the visualization of the presence of contrast agent content like that of iodine, barium, gadolinium, gold or other chemical elements. Other examples are the generation of separate 3D volumes of material densities containing water-like tissue, bone mineral, and/or K-edge contrast material. All these methods work better the stronger the spectral separation of the acquired projections is. Dependent on the chosen methods, the number of separated physical/chemical properties or the number of distinguishable materials also depend on the number of different spectra used for the projection generation.

SUMMARY

Aspects of the present application address the above-referenced matters and others.

In accordance with aspects of the present disclosure, an X-ray imaging system is presented. The X-ray imaging system includes an X-ray device having a single X-ray source for forming a plurality of X-ray beams, a filter positioned within the plurality of X-ray beams, an object space where the object to be imaged is accommodated, and an X-ray detector including an array of a plurality of pixels.

The X-ray device, the filter, and the plurality of pixels are configured such that at least one pixel is exposed to the plurality of X-ray beams. X-ray radiation received by a particular pixel undergoes a same spectral filtration by the filter. Pixels receiving the X-ray radiation undergoing the same spectral filtration are summarized to a pixel subset. At least two subsets of pixels exist.

According to an aspect of the present disclosure, the X-ray device includes a collimator positioned between the X-ray device and the filter, the collimator having a plurality of openings for directing the plurality of X-ray beams generated by the X-ray source.

According to a further aspect of the present disclosure, the X-ray source includes an X-ray emission area with a spatially modulated X-ray intensity profile such that the plurality of X-ray beams originate from one or more pronounced intensity maxima of the X-ray emission area.

According to another aspect of the present disclosure, the plurality of pixels have X-ray insensitive regions therebetween. The X-ray imaging system and the collimator are configured to reduce X-ray intensity in the X-ray insensitive regions between the plurality of pixels.

According to yet another aspect of the disclosure, the filter includes at least two different materials. In one exemplary embodiment, one of the filter materials is air.

According to yet another aspect of the disclosure, the filter includes one material having a spatial modulation. In one exemplary embodiment, the filter is a combination of at least two spatially separated filters.

According to yet another aspect of the disclosure, the filter has a spatially alternating pattern of spectral filtration. The filter is a grating having grating lines or a pattern of tiles representing different spectral filtration. In one exemplary embodiment, the filter is replaceable and can be chosen from a set of a plurality of different filters.

According to yet another aspect of the disclosure, the subsets of pixels of the X-ray detector form an interlacing and alternating pattern of rows, columns, or tiles. A smallest effective size of a row, a column, or a tile of the alternating pattern of a subset of pixels of the X-ray detector corresponds to the effective size of one pixel.

According to yet another aspect of the disclosure, the filter is configured such that at least one pixel subset represents an opaque filtration of X-rays such that at least one pixel subset of the plurality of pixels of the X-ray detector is shadowed from any direct X-ray radiation from the X-ray source of the X-ray device.

According to yet a further aspect of the disclosure, a method for measuring an intensity of scattered X-ray radiation for at least one pixel subset of an X-ray imaging system as described above is presented, the method including generating a plurality of X-ray beams via the X-ray device, transmitting the plurality of X-ray beams through a combination of one or more filters and collimators, as well as an object included in the X-ray imaging system, and detecting the scattered X-ray intensity for at least one pixel subset representing an opaque filtration of direct X-ray radiation from the X-ray device.

According to yet a further aspect of the disclosure, a method for generating at least one X-ray projection data set including at least two subsets of spectrally different X-ray projections with an X-ray imaging system is presented, the method including generating a plurality of X-ray beams via the X-ray device, transmitting the plurality of X-ray beams through a combination of one or more filters and collimators, as well as an object included in the X-ray imaging system, detecting the X-ray beams via the X-ray detector of the X-ray imaging system, and logically assigning the acquired data of the pixel subsets of the plurality of pixels of the X-ray detector to subsets of spectrally different X-ray projections.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

DETAILED DESCRIPTION

Figure 1:
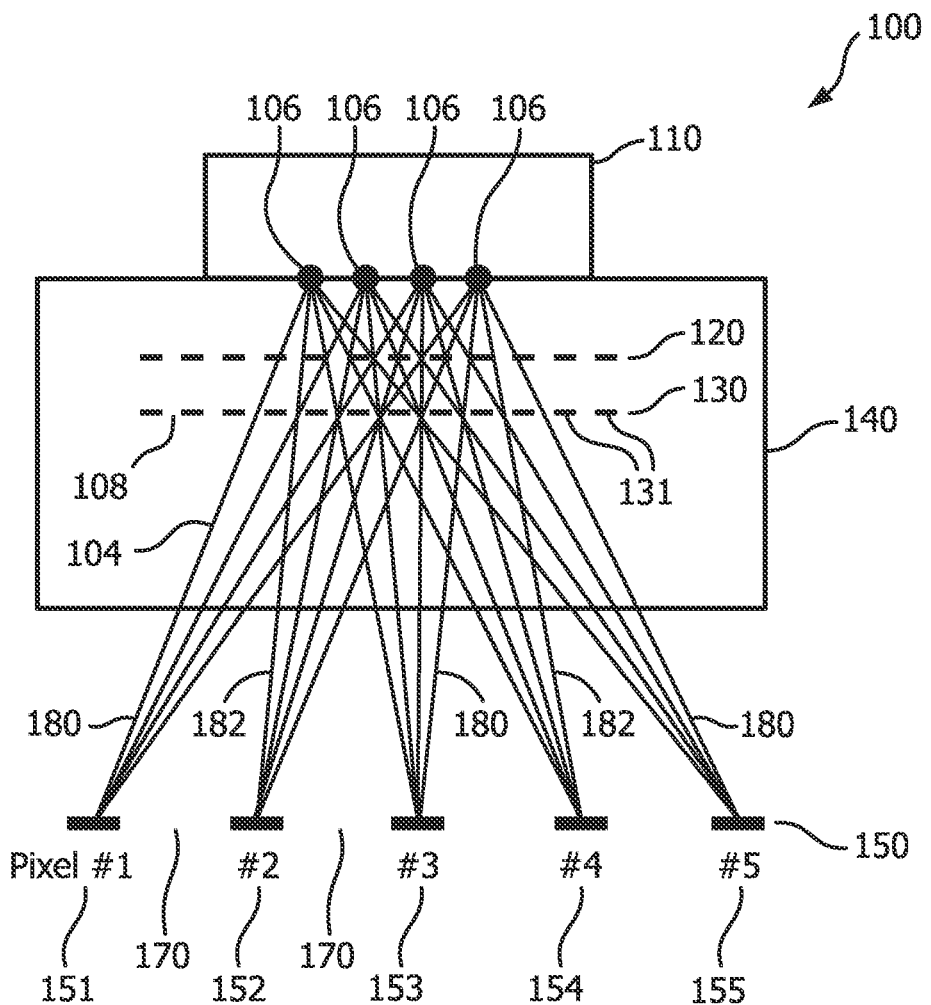
FIG. 1 illustrates an imaging geometry of an imaging system, according to the present disclosure.

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

Collecting many projections of an object and filtration of the x-ray beams are factors used in CT image formation. The present disclosure relates to an x-ray device, particularly in the form of a Computed Tomography (CT) scanner, which includes at least a radiation source, a beam filter, and a radiation-sensitive detector array, described below.

Special usage of spectral CT imaging may be seen in a device which provides different X-ray spectra for particular pixels. One might think that simply putting a spatially modulated filter into the X-ray beam might already provide such functionality by directly projecting the filter structures onto the image detector. Indeed, for a CT system with an ideal point-like X-ray source, such a filter may provide a desired spatially modulated X-ray spectrum.

However, one skilled in the art understands that this simple method is very often not suitable for the reason that a finite extension of the X-ray spot is present. In fact the spatial extension of the X-ray emitting area blurs the projected structures, i.e., projected filter structures are convolved by a penumbra, which depends on the geometric dimensions of the system. In most cases, the filter needs to be placed close to the X-ray source such that a desired spectrum for a particular direction cannot be limited to the size of a pixel within the detector without a massive overlap with neighboring pixels.

To overcome the penumbra problem, an approach is proposed which uses an array of almost point-like X-ray sources, in the sense that the spatial extension of these "point emitters" is so small that the penumbra effects in the detected image are limited to a broadening in the extension of a pixel size. In combination with a periodic array of filter materials, each point emitter projects the filter array onto the detector, such that the overlay of each particular image (using the periodicity of the arrays) produces a congruently superposed image of the filtered array. Thus, a system and method is suggested that includes introducing a filter which spatially and spectrally modulates the X-ray beam. This filter may be, for example, constructed from two different materials within an X-ray system in order to produce a spectrally modulated beam such that, for example, neighboring pixels of the X-ray detector receive different spectra.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Referring to FIG. 1, an imaging geometry of an imaging system having at least one X-ray source, according to the present disclosure is presented.

The X-ray imaging system 100 includes at least one X-ray device 110 emitting X-rays from a number of locations 106, a filter grating 120, an optional collimator grating 130, an object space 140, and an X-ray detector 150 including an array of a plurality of pixels 151 to 155, which may be separated by X-ray insensitive gaps 170. The X-ray device 110 generates a plurality of X-ray beams 104, each beam 104 characterized by connecting one of the locations 106 with one of the pixels 151 to 155, respectively. The X-ray beams 104 pass through a filter 120. The filter 120 may be referred to as a "filter grating" configured to apply a specific filtration to each of the X-ray beams 104. Locations 106, filter grating 120, and detector pixels 151 to 155 are configured such that all X-ray beams 104 connected to a particular single pixel undergo the same spectral filtration by filter grating 120.

The spectral and also spatial separation of X-ray beams 104 may be supported by an optional collimator grating 130 which includes a plurality of openings 108. The openings 108 are configured such that they allow for the passage of photons propagating along the center of each of the X-ray beams 104, or stated differently, each photon propagating from the center of a location 106 to the center of any pixel 151 to 155 passes an opening 108 of the optional collimator grating 130. Furthermore, blockings 131 of the optional collimator 130 are configured to suppress to a maximum amount of X-ray photons, which propagate from one of the locations 106 towards the gaps 170 in between the pixels 151 to 155.

Not illuminating the pixel gaps 170 means that an object or patient placed in the object space 140 receives less dose compared to a configuration in which the optional collimator grating 130 is not present. For ideal opaque gratings, even a total shadowing of the pixel gaps 170 can be achieved. It can be shown that the dose saving is about 20% for current CT geometries. It is contemplated that the collimator grating 130 is constructed or formed from highly opaque materials, such as, for example, Tungsten or Lead of appropriate thickness, such that the amount of transmitted radiation through the blockings 131 is reduced to a minimum. An object to be imaged is positioned in the object space 140 located (from the viewpoint of the X-ray source) behind the filter grating 120 and the optional collimator 130, but before the X-ray detector 150. In this exemplary embodiment, five pixels 151 to 155 are shown. However, one skilled in the art may envision several more pixels forming the array of the X-ray detector 150.

Figure 2A:
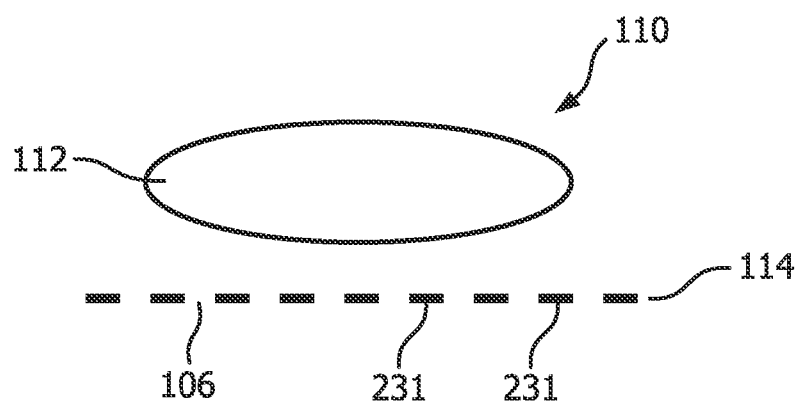
FIGS. 2a and 2b illustrate a side view and a top view, respectively, of the filter, according to the present disclosure.
Figure 2B:
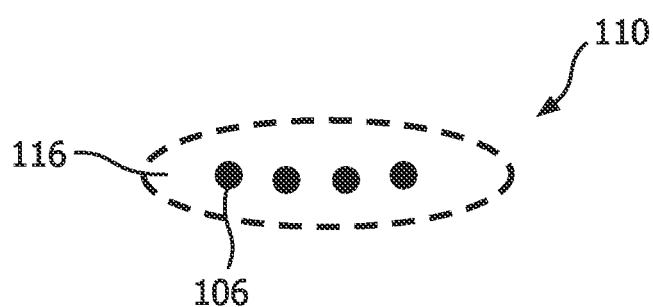

FIG. 2a and FIG. 2b show two possible configurations of the X-ray device 110. Both configurations provide locations 106 from which X-rays emerge. In FIG. 2a, the X-ray device 110 contains a single area 112 from which X-ray photons emerge. This area may be the common focal spot of a common X-ray tube. The emitted X-rays are collimated by a grating 114, which is configured to transmit X-rays only through its openings 106, which are therefore identical to the locations 106 of the X-ray device 110. It is contemplated that the grating 114 is constructed or formed from highly opaque materials, such as, for example, Tungsten or Lead of appropriate thickness, such that the amount of transmitted radiation through the blockings 231 is reduced to a minimum. It is noted that the X-ray beams 104 received by a particular pixel of detector 150 may pass only a particular number of locations 106, i.e., those locations 106 which are in the line-of-sight between a corresponding pixel of detector 150 and the X-ray emission area 112. Also it may be that X-ray beams 104 assigned to different pixels of detector 150 are assigned to completely different locations 106 of the X-ray device 110.

In an alternative embodiment shown in FIG. 2b, the X-ray device 110 includes a single area 116 from which X-ray photons emerge in a spatially modulated intensity such that the locations 106 are represented by local intensity maxima of the X-ray area 116. The area 116 may be the focal spot of an X-ray tube for which the modulation of X-ray intensity is performed by a correspondingly varying density of electrons hitting the metal anode. For example, the electrons may be generated from a spatially modulated electron source, and a common electron lens optics produces an "image" of the electron source, such that the focal spot displays the same spatial X-ray intensity pattern as the electron source area.

The filter 120 forms a characteristic pattern of different X-ray filtration. For example, referring to FIGS. 3a and 3b, this pattern may be in the form of alternating stripes that extend a horizontal (or vertical) length of the filter 120. The filter 120 is shown in a side view in FIG. 3a, where a first grating 210 and a second grating 220 are shown both differing from each other by different X-ray filtration properties. The filter 120 is shown in a top view in FIG. 3b, where the first grating 210 and the second grating 220 are shown extending a length of the filter 120.

This alternating pattern design of the filter 120 allows for alternating pixels of the plurality of pixels 151 to 155 to be illuminated with different X-ray spectra. For example, as shown in all of FIG. 1, FIG. 4, and FIG. 5, the first pixel 151 receives a first spectra 180 and the second pixel 152 receives a second spectra 182. Additionally, the third pixel 153 and the fifth pixel 155 receive the first spectra 180, whereas the fourth pixel 154 receives the second spectra 182. Stated differently, the odd pixels (i.e., pixels 151, 153, and 155)

receive the first spectra 180, whereas the even pixels (i.e., pixels 152 and 154) receive the second spectra 182. Thus, each adjacent or neighboring pixel may receive different spectra (i.e., creation of an alternating configuration of spectra). Stated differently, spectrum separation may be achieved. Moreover, the first spectra 180 may have a strong weight on high energy photons, whereas the second spectra 182 may have a strong weight on low energy photons, and vice versa.

As a result, by incorporating filter 120 into the imaging system 100, alternating pixels of the array of the X-ray detector 150 may receive different spectra. Thus, together with the arrangement of the X-ray emitting locations 106 of the X-ray device 110, the filter 120 causes the generation of at least two spectra, such that no spatial overlap between the spectrum occurs, or the spatial spectrum overlap is reduced to a minimum for particular locations on the X-ray detector 150.

It is noted that a pattern used for a filter grating 120 needs to be aligned to the pattern of the X-ray emission locations 106 of the X-ray device 110, to the pattern of the optional collimator grating 130, and the geometry of the pixel array of the X-ray detector 150. Thus, subsets of pixels are assigned for the X-ray detector 150, which are aligned to the pattern of different X-ray spectra. For example, the grating-line pattern of the filter grating 120 reported in FIGS. 3a and 3b would be used together with a similar grating-line pattern of the X-ray emission locations 106 of the X-ray device, optionally a grating-line pattern of the collimator grating 130, and a rectangular pattern of detector pixels of the X-ray detector 150 where subsets of pixels form an interlacing grating-line pattern.

Figure 3A:
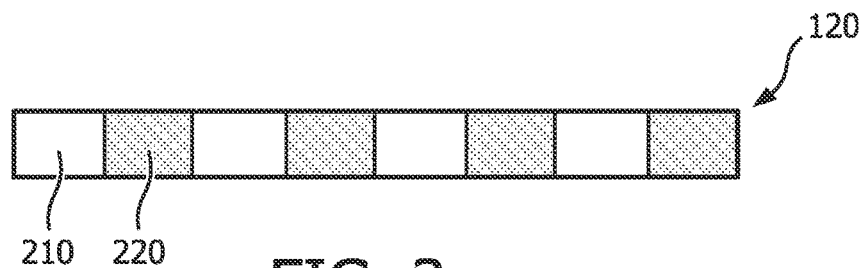
FIGS. 3a and 3b illustrate possible configurations of the X-ray filter passed by a plurality of X-ray beams, according to the present disclosure.
Figure 3B:
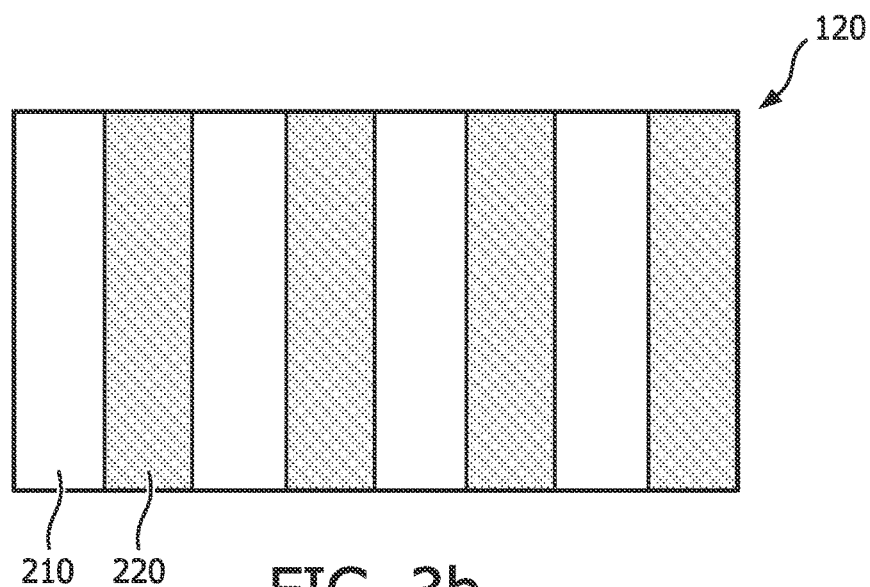
Figure 3C:
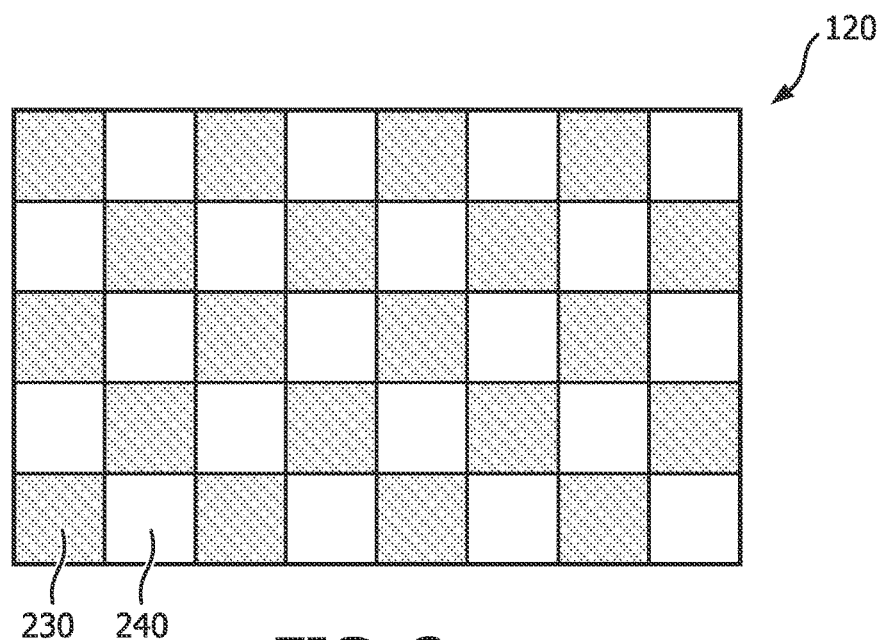
FIG. 3c illustrates an alternative arrangement of the filter passed by a plurality of X-ray beams, according to the present disclosure.

One skilled in the art will recognize that there are many more possibilities of pattern arrangement than those displayed in FIGS. 3a and 3b. An alternative arrangement is, for example, shown in FIG. 3c where the filter grating 120 is formed by a two-dimensional pattern of rectangular tiles 230, 240. This tile pattern is used together with an X-ray device 110 having X-ray emission locations 106 arranged in rectangular array of almost point emitters, optionally with a collimator grating 130 having a rectangular array of openings 108, and an X-ray detector 150 with a rectangular pixel matrix with pixel subsets forming interlacing tile patterns.

Referring back to FIG. 1, a detector pixel array is shown configured to detect the alternating pattern of spectral filtration, i.e., each pixel detects a spectrum different from its direct neighboring pixel. However one skilled in the art will recognize that other configurations are possible. For example, the X-ray device 110, the filter grating 120, and the optional collimator grating 130 may be configured in a way that the first spectra 180 and second spectra 182 form an interlacing pattern with a larger periodicity such that a column, a row, or a tile of the pattern covers an detector area with size dimensions larger than that of a single detector pixel. This means that the subsets of pixels may contain sequences of directly neighboring pixels. In other words, the size of a column, a row or a tile of the pattern represented by the subsets of pixels may correspond to the size of one pixel, but it is not limited to the size of one pixel and may therefore have a larger size.

Further, while only means for the first spectra 180 and the second spectra 182 are shown in FIG. 1, it is understood for one skilled in the art that the X-ray device 110, the filter grating 120, and the optional collimator grating 130 and the detector 150 may be configured in a way that interlacing patterns with more than two spectra can be generated. For example, by choosing a filter grating providing means for three or more different X-ray filtrations and having appropriate grating pitches, it is possible to generate an alternating and interlacing sequence of three or more different spectra on the detector 150.

Figure 4:
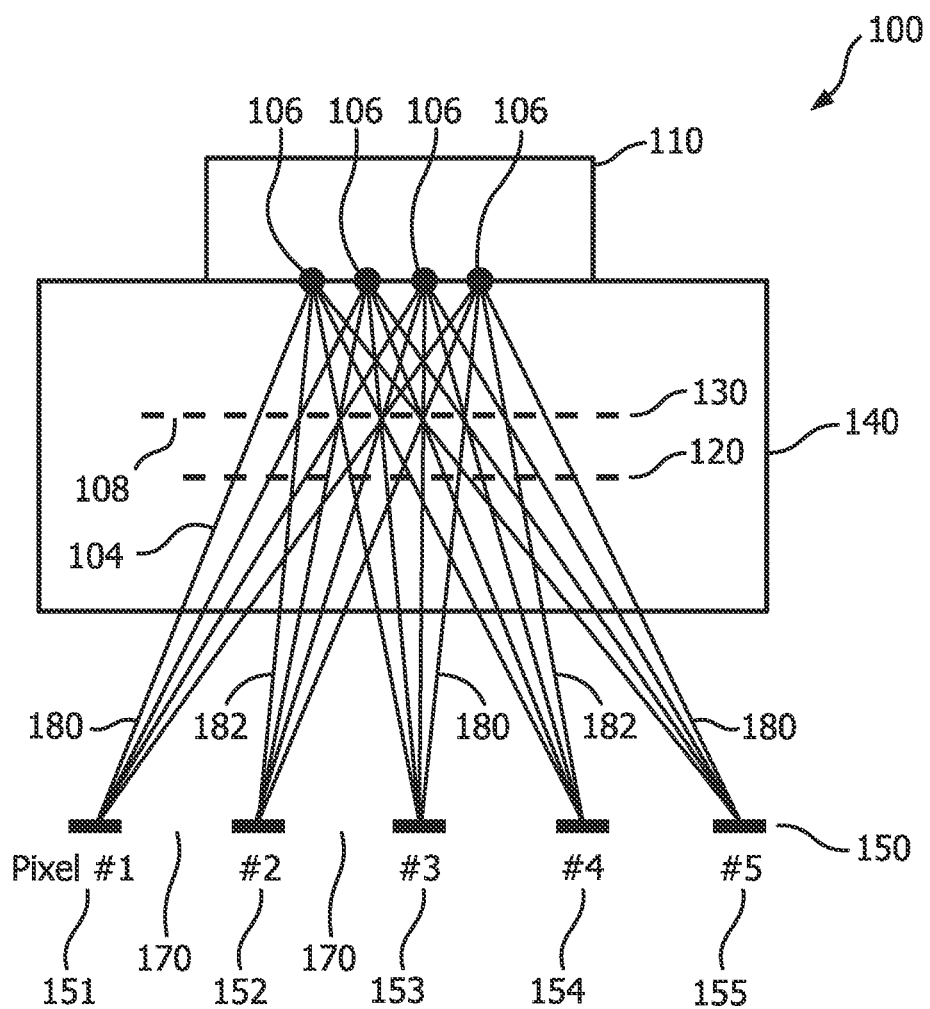
FIG. 4 illustrates an alternative positioning of the filter grating, according to the present disclosure.
Figure 5:
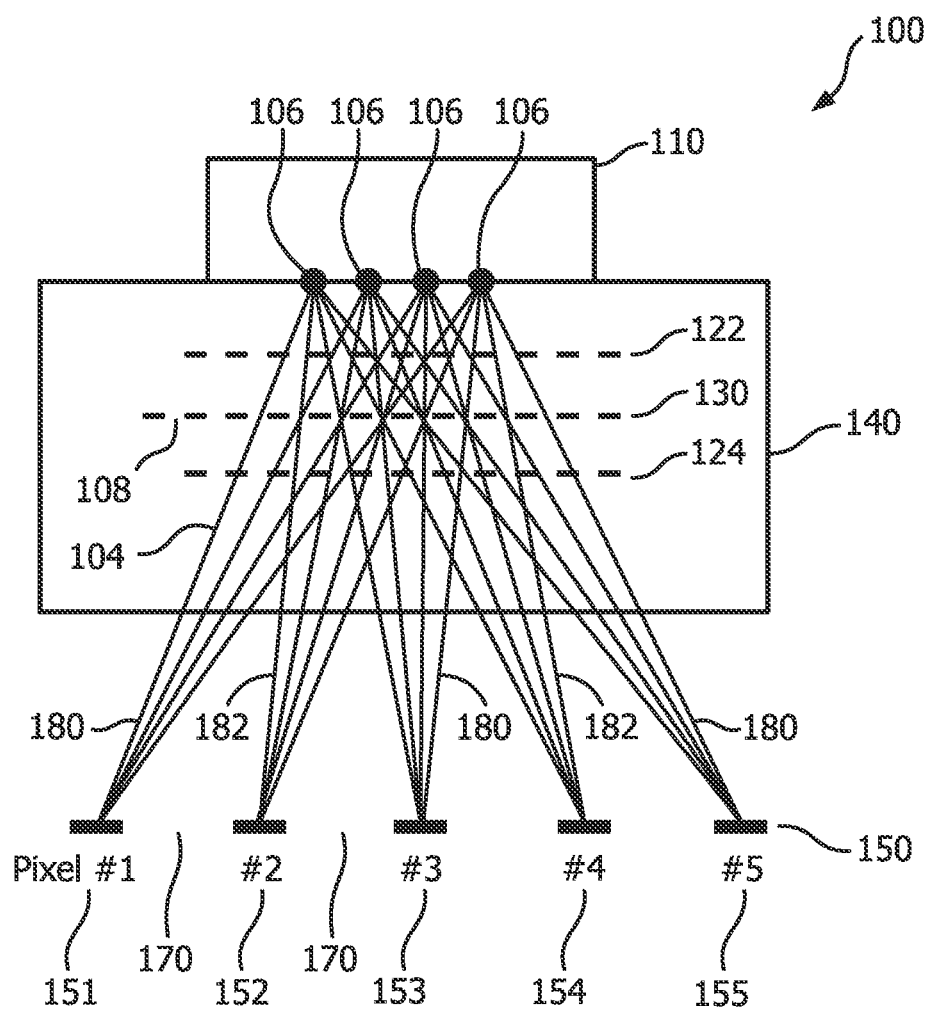
FIG. 5 illustrates an alternative of the filter grating being replaced by a combination of two or more filters, according to the present disclosure.

It is noted that a filter 120 fulfilling the configuration (i.e., by choosing an appropriate geometry) may be placed at different positions between X-ray device 110 and detector 150. For example, FIG. 4 shows an alternative positioning of the filter grating 120 (it is noted that the grating pitch needs to be adapted according to the total system geometry). Also, there is no fixed order in which, for example, the filter grating 120 and the optional collimator grating 130 have to be mounted into the system. As an alternative embodiment, the filter grating 120 may be replaced by a combination of two or more filters 122 and 124 as shown, for example, in FIG. 5. One skilled in the art may envision several more arrangements and patterning of an effective grating 120.

The filter 120 may include or be formed of two or more different materials. Alternatively, the filter 120 may be formed from a single material providing different filtration by a modulation of the material thickness. One of the filter materials may be air or another weakly attenuating material. Effectively, this weakly attenuating material represents an effective zero attenuation of X-rays such that one of the subsets of pixels is assigned to an effectively unfiltered spectrum.

Further, one or more of the materials of the filter grating 120 may be formed of materials with relatively large K-edge energies, such as tantalum, tungsten, or lead which results in spectra filtration with a relatively enhanced transmission of photons with energies below the K-edge. The K-edge may be chosen high enough such that photons with energies below the K-edge may still pass the object placed in the object space 140. Using materials with a relatively low K-edge such as aluminum, copper or tin are also contemplated to create spectra which put more relative weight to "high" energies, since it is assumed that their K-edge energy is that low that photon energies below their K-edge will effectively not be able to transmit the object placed into the object space 140. There are many more conceivable embodiments that enable access to spectral CT capabilities without the need of highly specialized detectors (e.g., photon-counting or multi-layer detectors) or tubes with fast switching capabilities.

Additionally, one or more materials (or their thickness) of filter grating 120 may be made opaque for X-rays, such that at least one subset of pixels does not get illuminated by primary radiation. Consequently, radiation received by these pixels consists of scattered radiation only. By interpolation, the intensity received by the fully illuminated pixels may be corrected for by its scatter content.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure. Therefore, the above description should not be construed as limiting, but merely as exemplifications of particular embodiments. Those skilled in the art will envision other modifications within the scope and spirit of the claims appended hereto.

What is claimed is:

1. An X-ray imaging system for generating X-ray projections of an object, the X-ray imaging system comprising:
    an X-ray device having a single X-ray source for forming a plurality of X-ray beams;
    a filter configured to be positioned within the plurality of X-ray beams;
    an object space where the object to be imaged is to be accommodated; and
    an X-ray detector including an array of a plurality of pixels;
    wherein the X-ray device, the filter, and the plurality of pixels are configured such that at least two pixels are to be exposed to the plurality of X-ray beams;
    wherein X-ray radiation of the plurality of X-ray beams which is to be received by a particular pixel is to undergo a same spectral filtration by the filter;
    wherein pixels which are to receive the X-ray radiation undergoing the same spectral filtration are part of a same pixel subset;
    wherein at least two subsets of pixels are to exist,
        wherein the plurality of pixels have X-ray insensitive regions therebetween, and a collimator having a plurality of openings, and
        wherein the X-ray imaging system and the collimator are configured to reduce X-ray intensity in the X-ray insensitive regions between the plurality of pixels.

2. The X-ray imaging system of claim 1, wherein the X-ray device includes a collimator positioned between the X-ray device and the filter, the collimator having a plurality of openings for directing the plurality of X-ray beams generated by the X-ray source.

3. The X-ray imaging system of claim 1, wherein the X-ray source configured to include an X-ray emission area with a spatially modulated X-ray intensity profile such that the plurality of X-ray beams originate from one or more pronounced intensity maxima of the X-ray emission area.

4. The X-ray imaging system as in claim 1, wherein the filter includes at least two different materials.

5. The X-ray imaging system as in claim 4, wherein one of the at least two different materials is air.

6. The X-ray imaging system as in claim 1, wherein the filter includes one material having a spatial modulation.

7. The X-ray imaging system as in claim 1, wherein the filter is a combination of at least two spatially separated filters.

8. The X-ray imaging system as in claim 1, wherein the filter has a spatially alternating pattern of spectral filtration.

9. The X-ray imaging system as in claim 8, wherein the filter is a grating having grating lines or a pattern of tiles representing different spectral filtration.

10. The X-ray imaging system as in claim 1, wherein the filter is replaceable and chosen from a set of a plurality of different filters.

11. The X-ray imaging system as in claim 1, wherein the subsets of pixels of the X-ray detector form an interlacing and alternating pattern of rows, columns, or tiles.

12. The X-ray imaging system as in claim 11, wherein a smallest effective size of a row, a column, or a tile of the alternating pattern of a subset of pixels of the X-ray detector corresponds to the effective size of one pixel.

13. The X-ray imaging system as in claim 1, wherein the filter is configured such that at least one pixel subset represents an opaque filtration of X-rays such that at least one pixel subset of the plurality of pixels of the X-ray detector is shadowed from any direct X-ray radiation from the X-ray source of the X-ray device.

14. A method for measuring an intensity of scattered X-ray radiation for at least one pixel subset of an X-ray imaging system as in claim 13, the method comprising:
    generating a plurality of X-ray beams via the X-ray device;
    transmitting the plurality of X-ray beams through a combination of one or more filters and collimators, as well as an object included in the X-ray imaging system; and
    detecting the scattered X-ray intensity for the at least one pixel subset representing an opaque filtration of direct X-ray radiation from the X-ray device.

15. A computed tomography system using a method as in claim 14.

16. A method for generating at least one X-ray projection data set including at least two subsets of spectrally different X-ray projections with an X-ray imaging system as in claim 1, the method comprising:
    generating a plurality of X-ray beams via the X-ray device;
    transmitting the plurality of X-ray beams through a combination of one or more filters and collimators, as well as an object included in the X-ray imaging system;
    detecting the X-ray beams via the X-ray detector of the X-ray imaging system; and
    assigning the acquired data of the pixel subsets of the plurality of pixels of the X-ray detector to subsets of spectrally different X-ray projections.

17. A method for generating at least one X-ray projection data set corrected for scattered X-ray radiation using a method to measure the intensity of scattered X-ray radiation and correcting at least one X-ray projection data set as generated with a method as in claim 16 for scattered X-ray radiation.

18. A method for generating at least one 2D data set or at least one 3D data set representing chemical or physical information of an object using at least one X-ray projection data set generated by any of the methods as in claim 16.

19. A method as in claim 18, wherein the chemical or physical information of at least one 2D data set or at least one 3D data set is one of the following:
    a representation of particular chemical elements or chemical compositions, in units of beam attenuation, mass densities, concentrations, or Hounsfield units;
    a combination of particular chemical elements or chemical compositions, in units of beam attenuation, mass densities, concentrations, or Hounsfield units;
    a combination of particular chemical elements or chemical compositions subtracted by another combination of particular chemical elements or chemical compositions, in units of beam attenuation, mass densities, concentrations, or Hounsfield units;
    a ratio of beam attenuation, mass densities, concentrations, or Hounsfield units of one combination of particular chemical elements or chemical compositions relative to another combination of particular chemical elements or chemical compositions; and
    a representation of the object processed such as if monochromatic X-ray radiation had been used for imaging.

20. An X-ray imaging system for generating X-ray projections of an object, the X-ray imaging system comprising:
    an X-ray device having a single X-ray source for forming a plurality of X-ray beams;
    a filter configured to be positioned within the plurality of X-ray beams;
    an object space where the object to be imaged is to be accommodated; and an X-ray detector including an array of a plurality of pixels;
wherein the X-ray device, the filter, and the plurality of pixels are configured such that at least two pixels is to be exposed to the plurality of X-ray beams;
wherein X-ray radiation of the plurality of X-ray beams which is to be received by a particular pixel is to undergo a same spectral filtration by the filter;
wherein pixels which are to receive the X-ray radiation undergoing the same spectral filtration are part of a same pixel subset;
wherein at least two subsets of pixels are to exist, and
wherein the filter is configured such that at least one pixel subset represents an opaque filtration of X-rays such that at least one pixel subset of the plurality of pixels of the X-ray detector is shadowed from any direct X-ray radiation from the X-ray source of the X-ray device.

* * * * *